(12) United States Patent
Cadio et al.

(10) Patent No.: US 11,918,358 B2
(45) Date of Patent: Mar. 5, 2024

(54) TEST STRIP EJECTOR FOR MEDICAL DEVICE

(71) Applicant: Roche Diabetes Care, Inc., Indianapolis, IN (US)

(72) Inventors: Michel Alain Jean Marie Cadio, Carmel, IN (US); Ahmet Konya, Ludwigshafen am Rhein (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 602 days.

(21) Appl. No.: 17/031,387

(22) Filed: Sep. 24, 2020

(65) Prior Publication Data

US 2022/0087582 A1 Mar. 24, 2022

(51) Int. Cl.
*A61B 5/15* (2006.01)
*A61B 5/145* (2006.01)
*A61B 5/151* (2006.01)
*G01N 33/487* (2006.01)

(52) U.S. Cl.
CPC .... *A61B 5/150358* (2013.01); *A61B 5/14532* (2013.01); *A61B 5/15016* (2013.01); *A61B 5/15113* (2013.01); *A61B 5/15126* (2013.01); *G01N 33/4875* (2013.01)

(58) Field of Classification Search
CPC .......... A61B 5/150358; A61B 5/14532; A61B 5/15016; A61B 5/15113; A61B 5/15126; G01N 33/4875
See application file for complete search history.

(56) References Cited

U.S. PATENT DOCUMENTS

| | | | |
|---|---|---|---|
| 8,715,571 B2 | 5/2014 | Hanson | |
| 8,828,330 B2 | 9/2014 | Galasso | |
| 9,933,409 B2 | 4/2018 | Wittekind, III | |
| 10,010,273 B2 | 7/2018 | Sloan | |
| 10,139,391 B2 | 11/2018 | Hou | |
| 2012/0143085 A1 | 6/2012 | Sauers et al. | |
| 2013/0143246 A1 | 6/2013 | Nelson et al. | |
| 2014/0001044 A1 | 1/2014 | Ecoff et al. | |
| 2014/0219712 A1 | 8/2014 | Bishop et al. | |
| 2017/0212096 A1* | 7/2017 | Hanson | G01N 33/4875 |
| 2018/0095035 A1 | 4/2018 | Wu | |
| 2020/0221983 A1 | 7/2020 | Taub | |

FOREIGN PATENT DOCUMENTS

| | | |
|---|---|---|
| EP | 2786139 B1 | 2/2016 |
| WO | 2014072370 A1 | 5/2014 |

OTHER PUBLICATIONS

International Search Report dated Dec. 13, 2021; PCT/US2021/051629; 12 pages.

* cited by examiner

*Primary Examiner* — Dennis White (57) ABSTRACT

A test strip eject mechanism for a fluid testing device comprising an actuation button and a lever having a distal end movably engaged with the button, the lever configured to rotate about a fulcrum, wherein the lever has a proximal end movably engaged with a sled which slides to transport the test strip, the device configured such that a user's insertion of a test strip onto the sled and in an insertion direction into the device causes the sled to contact the lever arm and the lever arm to contact and move the actuation button in an outward direction of the medical device and into a position where the actuation button can be actuated by the user.

26 Claims, 10 Drawing Sheets

TEST STRIP EJECTOR FOR MEDICAL DEVICE

FIELD

The present disclosure relates to a system and method for measuring a sample such as a body fluid, and more particularly to a device and method for loading and then ejecting an analyte test strip following measurement.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. Blood glucose meters use a test strip that receives a blood sample of the patient. The test strip has electrical contacts on the strip that are electrically contacted when the test strip is inserted into the meter. The meter determines a blood glucose level by measuring currents passed through the electrical contacts of the strip, and provides for readout of the glucose level.

Known meters receive the test strip in an insertion direction that also engages the electrical strip conductors of the test strip with the electrical contacts of the meter. As the test strip is loaded by the user, the insertion motion is used to drive the electrical contacts of the test strip into engagement with the contacts of the meter. A strip ejection system can provide for ejection of a dosed test strip following testing.

Some of the test strip eject mechanisms known in the art provide for a linear motion of a slide mechanism and a spring which is used to pull or retract the slide mechanism back. Such designs typically rely on the spring to pull the eject button back to a "ready to eject" position. Other test strip eject mechanisms utilize a rotational cam acting on a sled to eject a test strip.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY OF THE INVENTION

In a first aspect of the present disclosure, a fluid testing medical device is provided, comprising a test strip eject mechanism comprising a sled for receiving and transporting an analyte test strip, wherein the sled slides to transport the test strip into and out of contact with a connector of the medical device, the strip eject mechanism comprising an actuation button, a lever having a distal end movably engaged with the button, the lever configured to rotate about a fulcrum, wherein the lever further comprises a proximal end movably engaged with the sled, the device configured such that a user's insertion of a test strip onto the sled and in an insertion direction into the device causes the sled to contact the lever arm and the lever arm to contact and move the actuation button in an outward direction of the medical device and into a position where the actuation button can be actuated by the user.

In one embodiment of the first aspect, the sled of the device can be configured to move in a sled movement distance, the actuation button is configured to move in an actuation button distance, and the ratio of the sled movement distance to the actuation button distance is from 1 to 5.

In another embodiment of the first aspect, the ratio of the sled movement distance to the actuation button distance is from 3 to 5.

In another embodiment of the first aspect, the ratio of the sled movement distance to the actuation button distance is from 3.7 to 3.9.

In another embodiment of the first aspect, the device can include a lever lock which presses against and is frictionally engaged with the lever.

In another embodiment of the first aspect, the lever lock is further configured to press against and be frictionally engaged with the sled.

In another embodiment of the first aspect, the lever lock is further configured to press against and be frictionally engaged with the actuation button.

In another embodiment of the first aspect, the lever lock is further configured to press against and be frictionally engaged with the actuation button.

In another embodiment of the first aspect, the lever lock includes a tab that contacts the actuation button.

In another embodiment of the first aspect, the lever lock includes a tab that contacts the actuation button.

In a second aspect of the present disclosure, a fluid testing medical device is disclosed which comprises a test strip eject mechanism comprising a sled for receiving and transporting an analyte test strip, wherein the sled slides to transport the test strip into and out of contact with a connector of the medical device, the strip eject mechanism comprising an actuation button, a lever having a distal end movably engaged with the button, the lever configured to rotate about a fulcrum, wherein the lever further comprises a proximal end movably engaged with the sled, the device configured such that a user's actuation of the actuation button causes the actuation button to move the lever such that the lever rotates on its fulcrum and moves the sled in an outward direction to eject the test strip from the device.

In one embodiment of the second aspect, the sled of the device can be configured to move in a sled movement distance, the actuation button is configured to move in an actuation button distance, and the ratio of the sled movement distance to the actuation button distance is from 1 to 5.

In another embodiment of the second aspect, the ratio of the sled movement distance to the actuation button distance is from 3 to 5.

In another embodiment of the second aspect, the ratio of the sled movement distance to the actuation button distance is from 3.7 to 3.9.

In another embodiment of the second aspect, the device can include a lever lock which presses against and is frictionally engaged with the lever.

In another embodiment of the second aspect, the lever lock is further configured to press against and be frictionally engaged with the sled.

In another embodiment of the second aspect, the lever lock is further configured to press against and be frictionally engaged with the actuation button.

In another embodiment of the second aspect, the lever lock is further configured to press against and be frictionally engaged with the actuation button.

In another embodiment of the second aspect, the lever lock includes a tab that contacts the actuation button.

In another embodiment of the second aspect, the lever lock includes a tab that contacts the actuation button.

In a third aspect of the present disclosure, a method is provided of using a fluid testing medical device including a test strip eject mechanism including a sled for receiving and transporting an analyte test strip, wherein the sled is configured to slide to transport the test strip into and out of contact with a connector of the medical device, where the method includes configuring the strip eject mechanism to comprise an actuation button, a lever having a distal end movably engaged with the button, the lever configured to rotate about a fulcrum, wherein the lever further comprises a proximal end movably engaged with the sled; and inserting a test strip onto the sled and in an insertion direction into the device to thereby cause the sled to contact the lever arm and the lever arm to contact and move the actuation button in an outward direction of the medical device and into a position where the actuation button can be actuated by the user at a later time.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Specific embodiments of the present disclosure will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which embodiments of this invention belong. The terminology used herein is for describing particular embodiments only and is not intended to be limiting of the invention. As used in the specification and appended claims, the singular forms "a," "an," and "the" are intended to include the plural forms as well, unless the context clearly indicates otherwise.

Unless otherwise indicated, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention.

Methods and systems and parts thereof described herein can be combined to implement embodiments of the invention. Forms of words used herein can have variations: for example when a word such as "calculate" is used, this implies that variations such as "calculated" and "calculating" are understood and have been considered.

As used herein, "user," "patient," and "person" are used to refer to an individual interacting with the disclosed diabetes management systems to improve that individual's health via the improvements described herein.

As disclosed herein, a fluid analysis device (i.e., a health monitor device) includes an analyte test strip ejector configured to eject an analyte test strip from a test strip port of the device. An analyte test strip ejector may be useful, for example, where it is desirable to eject an analyte test strip containing a sample of bodily fluid, e.g., blood, following an analyte measurement conducted using the device. This allows a user of the device to dispose of the contaminated analyte test strip without touching the analyte test strip.

As noted herein, test strip ejectors and systems of the present disclosure can be used by individual users having fluid test devices such as the ACCU-CHEK® Guide System glucose meters manufactured by Roche. Test strip ejector systems of the present disclosure can also be incorporated in commercial devices, for example hospital meters, such as rechargeable test meters recharged by installation in a base unit, and/or blood glucose meters such as the ACCU-CHEK® Inform System glucose meters manufactured by Roche. The test strips used by such hospital and glucose test meters can be configured differently from the test strips discussed herein to conform to the requirements of the test and/or test meter, however the test strip ejector systems of the present disclosure can be similarly configured and function in a similar manner.

In addition, test strip ejectors and systems of the present disclosure can be incorporated into individual or commercial devices such as blood coagulant test meters, for example blood clotting time test meters such as the CoaguChek® XS System coagulant test meters manufactured by Roche Diagnostics. The test strips used by such blood coagulant test meters can be configured differently from the test strips identified herein to conform to the requirements of the test and/or test meter, however the test strip ejector systems of the present disclosure will be similarly configured and function in a similar manner.

Figure 1:
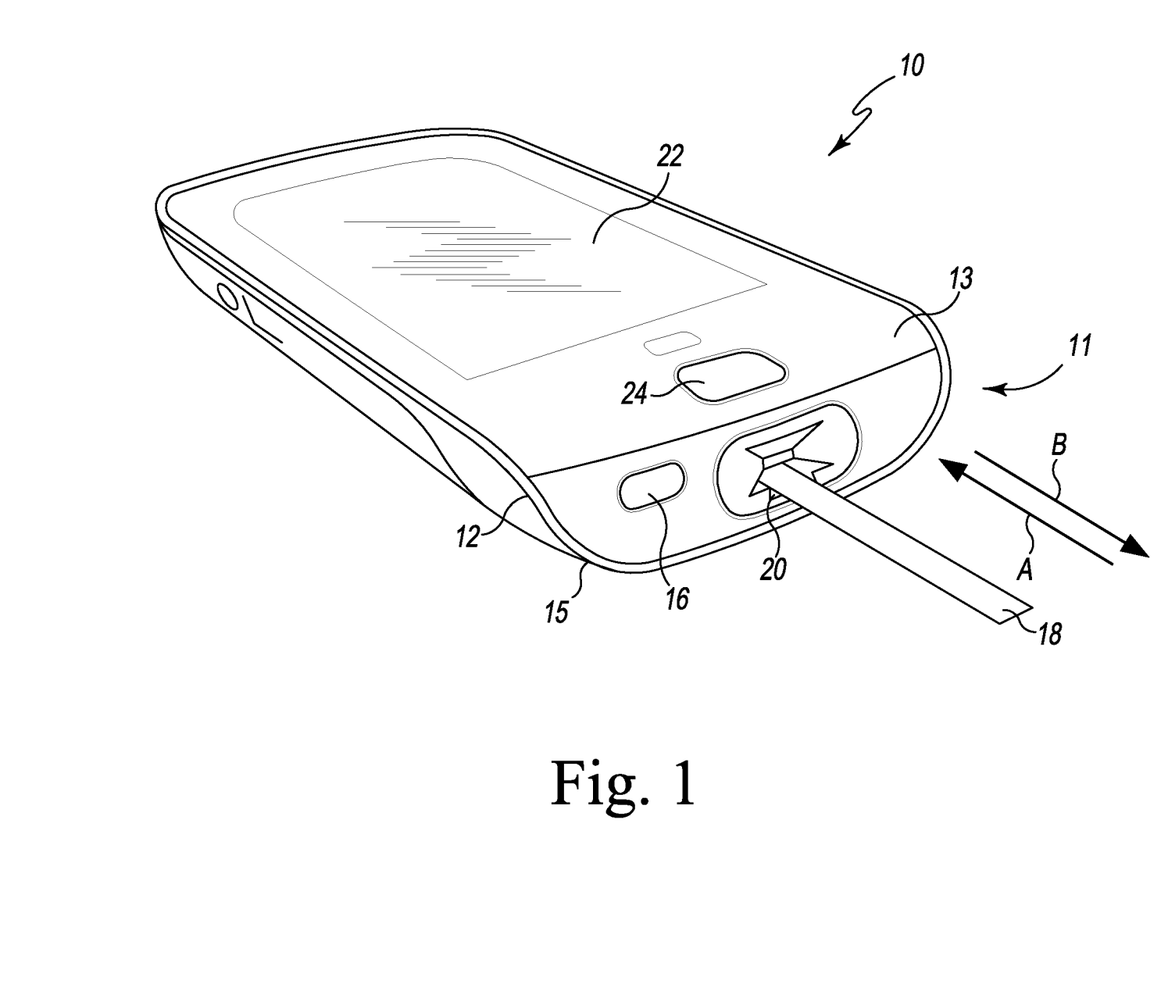
FIG. 1 shows a top perspective view of a fluid analysis device having a test strip ejector of the present disclosure.

Referring now to FIG. 1, an analysis device (health monitor device) 10 is shown. The device 10 can be used for example for testing blood glucose levels. The device in some embodiments can optionally be used as a remote controller of a medical device such as an insulin pump or continuous glucose monitor. As an example, the device 10 will be further described herein in an embodiment where the device serves as a controller for an insulin pump (not shown). In an embodiment, the device 10 can be constructed from a locked down smartphone, such as a locked down Android device. The device 10 includes a test strip ejector system 11 and a housing 12 comprising a top cover 13 and a bottom cover 15. The device 10 can include a graphical user interface 22 such as a touchscreen for calling up diabetes manager menus and displaying information. The device 10 can include a button 24 for providing further functionality, e.g., the button 24 can be used as an insulin button for confirming a previously set insulin delivery.

An ejection button (sometimes referred to herein as an ejector button or an actuation button) 16 is configured to be in a position ready to be actuated or pressed (i.e., in a "ready to eject" position) following completion of a test and ejection of a test strip which had previously been received in a loading direction "A" in housing 12. Upon depression of the ejection button 16, the test strip 18 is ejected in an ejection direction "B". In other words, after an analysis is undertaken, the ejection button 16 is in a position where it protrudes from the housing of the device and can be pressed by a user to eject the test strip. Alternately, it is possible that the user could manually pull the test strip 18 in the ejection direction "B" to manually remove the test strip, but this is not preferred since the user would be manually handling a previously dosed test strip.

Test strip 18 is slidably received via a test strip receiving port 20 provided in a first end of analysis device 10. The test strip receiving port 20 is sized to slidably receive the test strip 18 while generally preventing twisting or rotation, such as a racking rotation, due to lateral or side-to-side displacement of the test strip.

Figure 2:
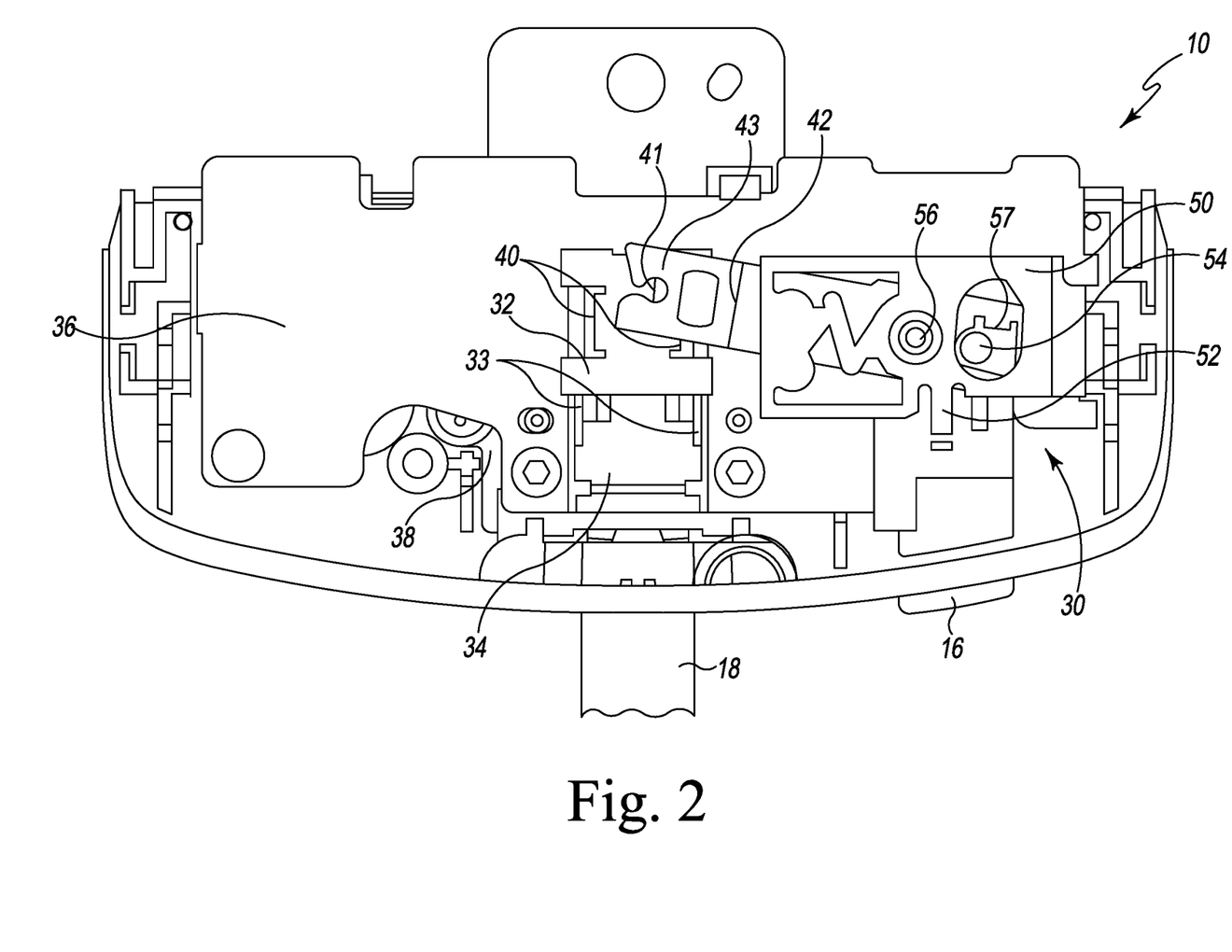
FIG. 2 is a plan view of the front end of the device, the view taken from below the device and with the bottom cover removed for clarity, showing a circuit board assembly and test strip ejector of the analysis device of FIG. 1, with the test strip ejector button and test strip ejector assembly shown in the ejection (ready to eject a test strip) position.
Figure 3:
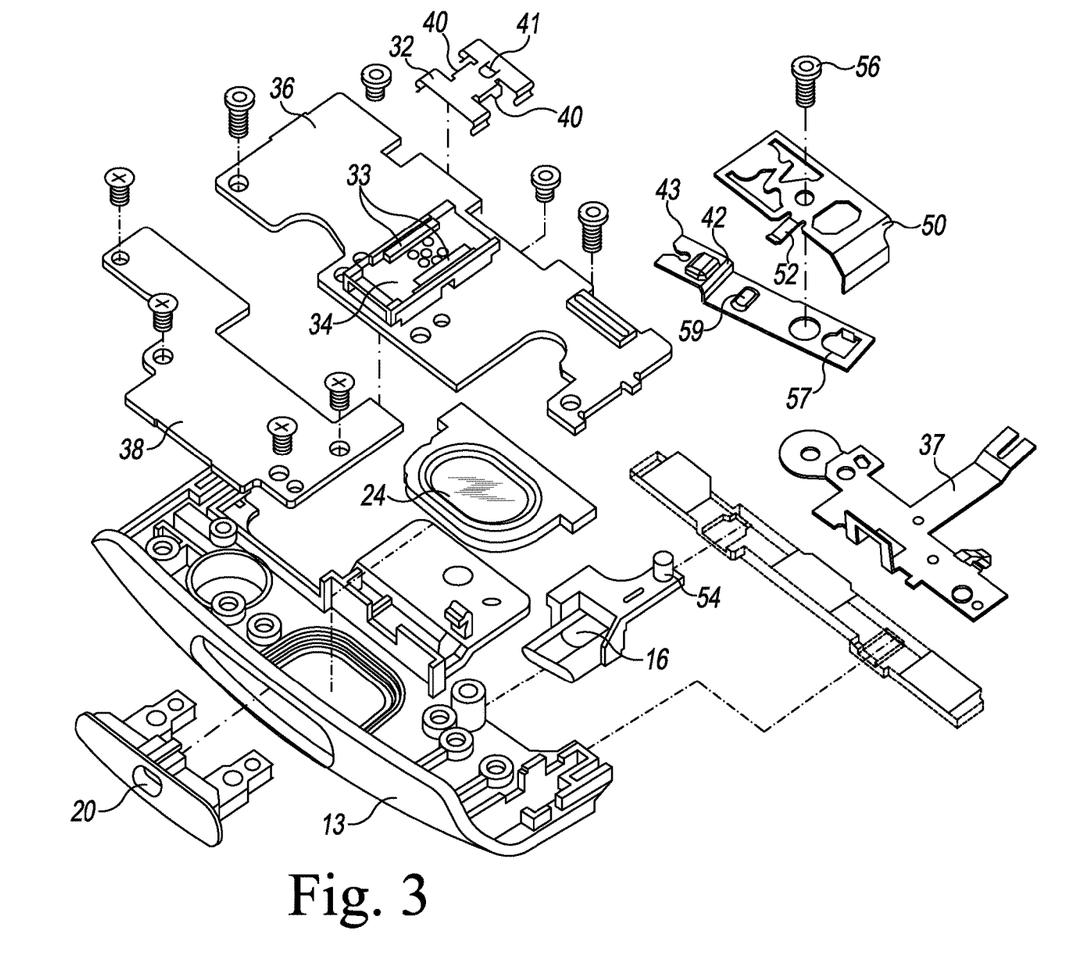
FIG. 3 is a partial exploded view of the analysis device of FIGS. 1 and 2.

Referring to FIGS. 2 and 3, with the bottom cover removed for clarity, the device 10 can include an embedded measurement engine firmware assembly 36 and a circuit board assembly 38 which are used to analyze the test strip analyte sample and provide other functionalities for the device, respectively. The test strip ejector button 16 and test strip ejector assembly 30 are shown in the ejection (ready to eject a test strip) position in FIG. 2.

Figure 4A:
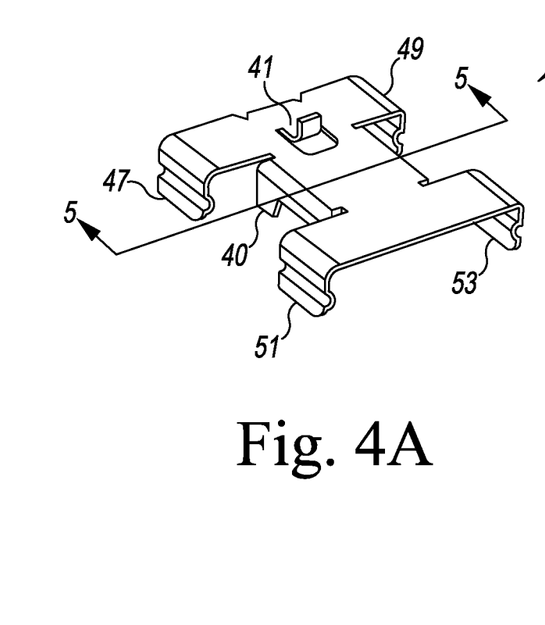
FIGS. 4A and 4B are perspective views of the test strip sled of the device.
Figure 4B:
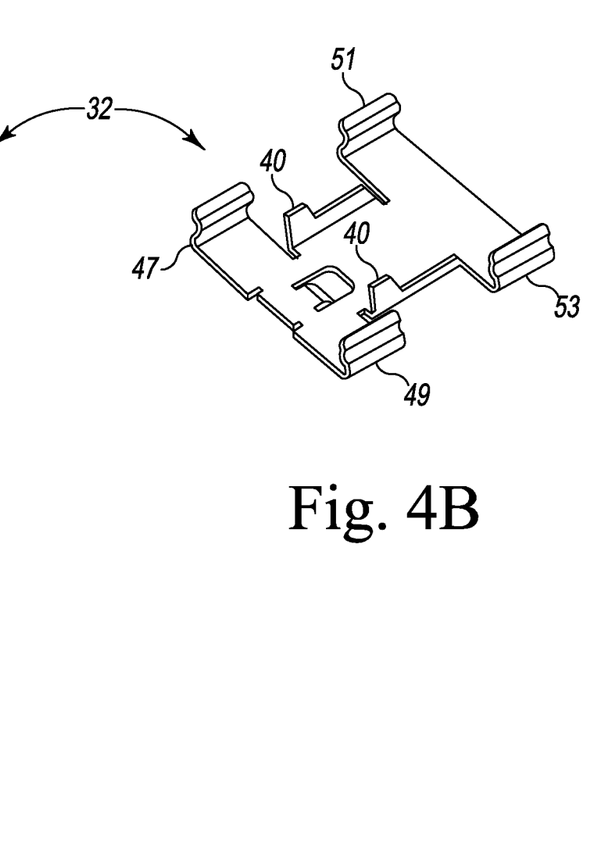
Figure 5:
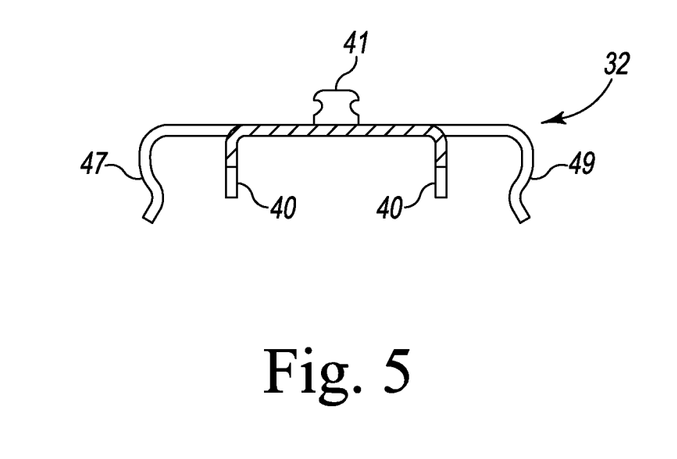
FIG. 5 is a cross-sectional view of the test strip sled taken along lines 5-5 of FIG. 4A.

The test strip ejector assembly 30 of the analyte device 10 comprises a sled 32 which is snapped onto a stationary test strip connector 34. The sled 32 is free in translation and can slide back and forth on the connector 34 along guide rails 33 of the connector. Referring to FIGS. 4A, 4B and 5, the sled 32 has contact legs 47, 49, 51, 53 which contact and ride along the guide rails 33 of the connector 34. An example of a test strip sled sliding along guide rails is disclosed in U.S. Pat. No. 8,715,571 B2, issued on May 6, 2014, which is incorporated by reference herein in its entirety.

As best shown in FIGS. 2, 3, 4A, 4B and 5, the sled 32 can include two tabs 40 protruding inside the connector 34. The tabs 40 can comprise a metal although other materials could be utilized such as polymeric or ceramic materials including plastics, ceramics, etc. The tabs 40 can occupy some of the space that the strip would normally occupy when fully inserted. The motion of inserting a test strip pushes against the tabs 40 and thus the sled 32 during insertion (if the sled 32 is not already pushed inward). The sled 32 comprises a third tab 41 bent away from the strip connector 34. This tab 41 is generally perpendicular to the axis of the sliding movement of the sled 32 relative to the connector 34 and is configured to provide contact surfaces for contacting a fork-like structure 43 provided on an eject lever 42. The third tab 41 of the sled 32 and the fork-like structure 43 of the eject lever 42 permit the translational motion of the sled 32 to be transmitted to a rotational movement of the eject lever 42 about its fulcrum and vice versa.

Referring to FIGS. 2, 3, 6A and 6B, the eject lever 42 can be constructed of a sheet metal but could be made of other materials such as other metals, or polymeric or ceramic materials. As mentioned above, the eject lever 42 comprises the fork 43 that straddles the third tab 41 of the sled 32 at one end of the eject lever 42, and comprises a hole or a slot 57 that is configured to receive a pin 54 of the eject button 16 at its other end. Between these two features of the eject lever 42, the eject lever 42 includes a round hole that receives (i.e., straddles) a fastener 56 (e.g., a round pin or screw) that connects it to the housing. This round hole receiving the round pin 56 provides the rotating axis of the eject lever 42 and the fulcrum point of the lever arm 42.

Referring to FIGS. 2 and 3, the eject button 16 is guided in the housing by guide rails that allow for the eject button 16 to slide inward and outward only. The eject button 16 also provides the pin 54 described above and which pin is captured or received by the hole 57 of the eject lever 42, providing a pin in slot connection between the two parts.

The insertion force applied through the test strip 18 to the tabs 40 of the sled 32 pushes the sled 32 inwardly by translational motion on the connector 34 until the strip 18 is engaged and makes electrical connections with the electrical contacts of the embedded measurement engine firmware assembly 36 (see FIGS. 2 and 3). This force and motion of the sled 32 are in turn transmitted to the eject lever 42 which is connected to the sled to thereby rotate the eject lever 42 on its fulcrum. The portion of the lever 42 on the opposite side of the fulcrum is connected through the pin of the ejection button 16 to the ejection button so that the moving force pushes the ejection button 16 in a linear motion outward in a direction different than the strip insertion direction and into a position where the button protrudes from the housing of the device and is thus, in a ready to eject position. In one embodiment, the ejection direction (ejection direction "B" as shown in FIG. 1) is in generally the opposite direction as the strip insertion direction (insertion direction "A" as shown in FIG. 1). Optionally, insertion of the test strip 18 into the strip connector of the device may start up the device 10 to prompt for an analyte sample application (e.g., blood). Once the eject button 16 is in the ready to eject position, the eject button can be pressed by a user to eject the test strip 18 after testing by applying a force and pushing the eject button 16 inwardly, thereby reversing the motion so that the tabs 40 of the sled 32 push the test strip 18 out of the connector and out of the device 10. Once the eject button has been pressed and the test strip ejected, the button is then positioned in a default/neutral position where the button is generally positioned inside the housing 12 of the device, and optionally, the button would be generally flush with the outside surface of the housing 12.

As is apparent from the present disclosure, it is advantageous that the test strip ejector assemblies disclosed herein do not require a spring to be utilized for placing the ejector assembly (e.g., an ejector actuation button) in a "ready to eject" position. In other words, the ejector assemblies do not rely on a spring which is set into a "cocked" position and no mechanism to release such a cocked ejector to later eject a test strip from the test strip port. It is advantageous since springs can lose their shape and stability over time. The test strip ejector assemblies disclosed herein are also advantageous for hygienic reasons because a user can simply press an actuation button to eject a test strip and thus, the user does not have to physically contact a dosed test strip to eject it. Further, test strip ejector assemblies disclosed herein are advantageous because in a neutral/default position, the actuation button is generally flush with the exterior of the device housing rather than protruding from the housing. It can be advantageous to not have a protruding actuation button in the neutral/default position so that inadvertent button actuations do not occur and so that the button does not "catch" against other surfaces such as a user's clothes in everyday use. Lastly, the actuation button is configured to be placed into a "ready to eject" position as a result of a test strip being inserted into the device as described earlier. Thus, the actuation button is advantageously placed in the "ready to eject" position at a point in time which is close to when a user will be wanting to press the actuation button to eject a dosed test strip.

In certain embodiments, the device can be configured such that the actuation button travels a shorter distance than the sled such that the actuation button can move a strip a suitable distance outwardly from the device in the ejection direction while also limiting the distance the actuation button protrudes out of the device when it is in a position ready for actuation at a later time by the user (the "ready to eject" position). In selected embodiments, the sled 32 can accordingly be configured to move in a sled movement distance, the actuation button 16 (eject button) can be configured to move in an actuation button distance, and the ratio of the sled movement distance to the actuation button distance can be configured to be from 1 to 5. In another embodiment, the ratio of these distances can be from 3 to 5. In a further embodiment, the ratio of these distances can be from 3.7 to 3.9.

Referring to FIGS. 2, 3, 7A and 7B, in an embodiment, there is also a lever lock (also sometimes referred to as a friction plate or frictional plate spring) 50 applied to (i.e., secured to) the lever 42 and the ejection button 16, keeping these ejection mechanism parts from moving to a position different from the position last utilized by the user, and thereby preventing the mechanism from rattling in the user's hand. The lever lock 50 holds the button and sled (and lever) in the position last utilized by the user to prevent rattling caused by shaking and carrying. The lever lock enables the button and sled mechanism to be quiet such as when a user is handling, shaking or carrying the device. This is accomplished by use of the lever lock 50 that applies sufficient force to the lever 42, the button and the sled to reduce the rattling noise that may otherwise be caused by freely moving parts. It is believed that rattling is typically perceived by users to be associated with lower quality devices.

Figure 6A:
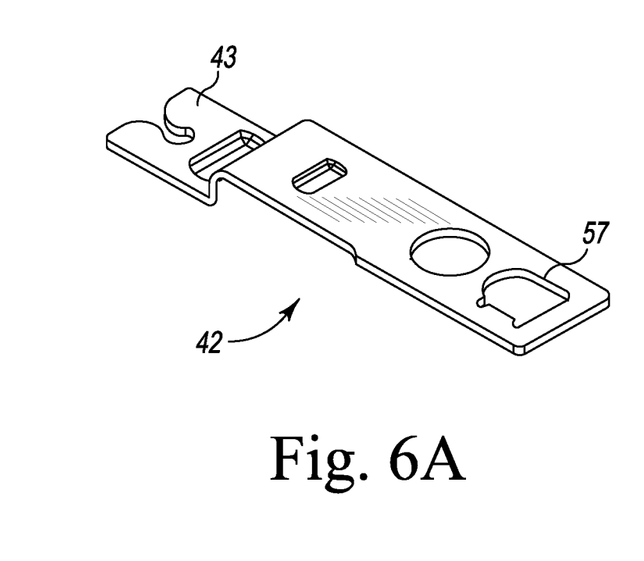
FIGS. 6A and 6B are perspective views of the eject lever of the device.
Figure 6B:
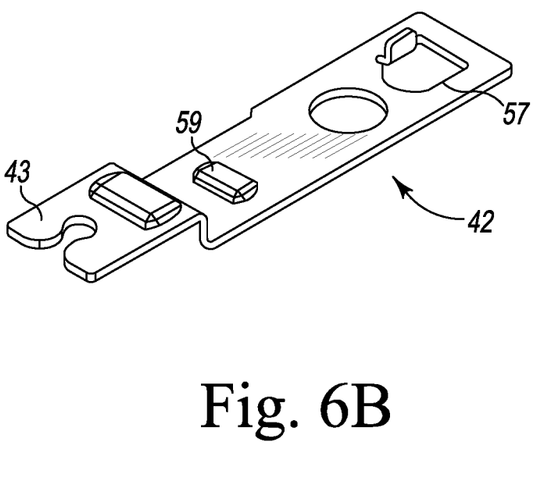

The lever lock 50 typically comprises a sheet metal, but the lever lock can also be made of other materials. The lever lock 50 is used as a lock to keep the eject lever 42 secured relative to the housing boss (fulcrum axis of the eject lever). With reference to FIGS. 3 and 6B, a bump or other protrusion 59 on the eject lever 42 can be provided to exert friction against the lever lock 50 while rotating and thus keep the mechanism from being loose. The lever lock 50 exerts a force on the eject lever 42 to provide a rattle minimization system, i.e., to provide sound reduction and minimize rattling (i.e., minimize extraneous movement) of the ejection assembly.

Figures 7A, 7B:
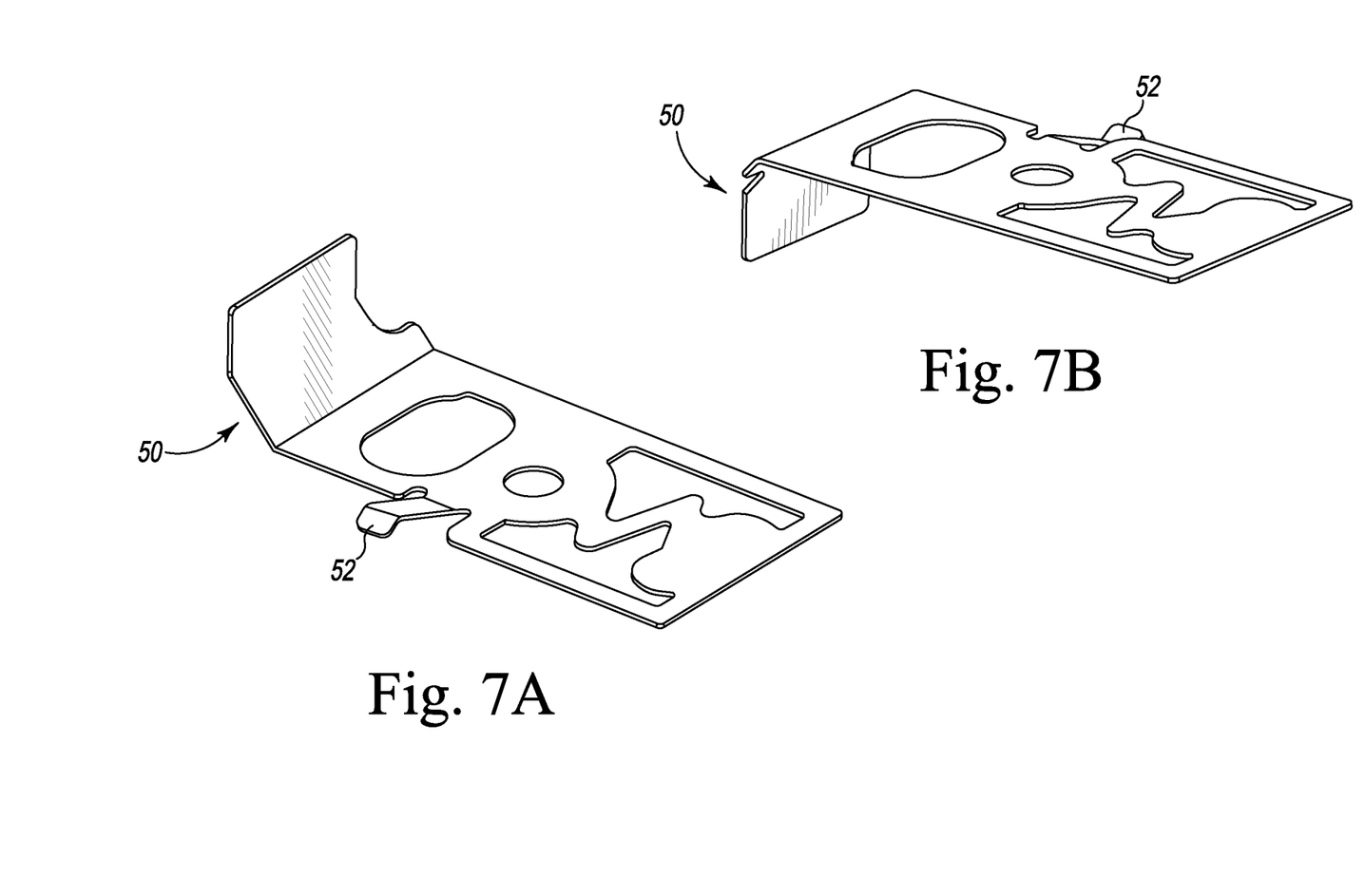
FIGS. 7A and 7B are perspective views of a lever lock in certain embodiments including the same.

In an embodiment, the lever lock 50 can include a tab 52 that contacts and frictionally engages the eject button 16 of the assembly to minimize rattling noise that would otherwise emanate from the eject button 16. The contact force provided by the tab 52 is high enough to prevent rattling noise emanating from the eject button 16.

Figure 8:
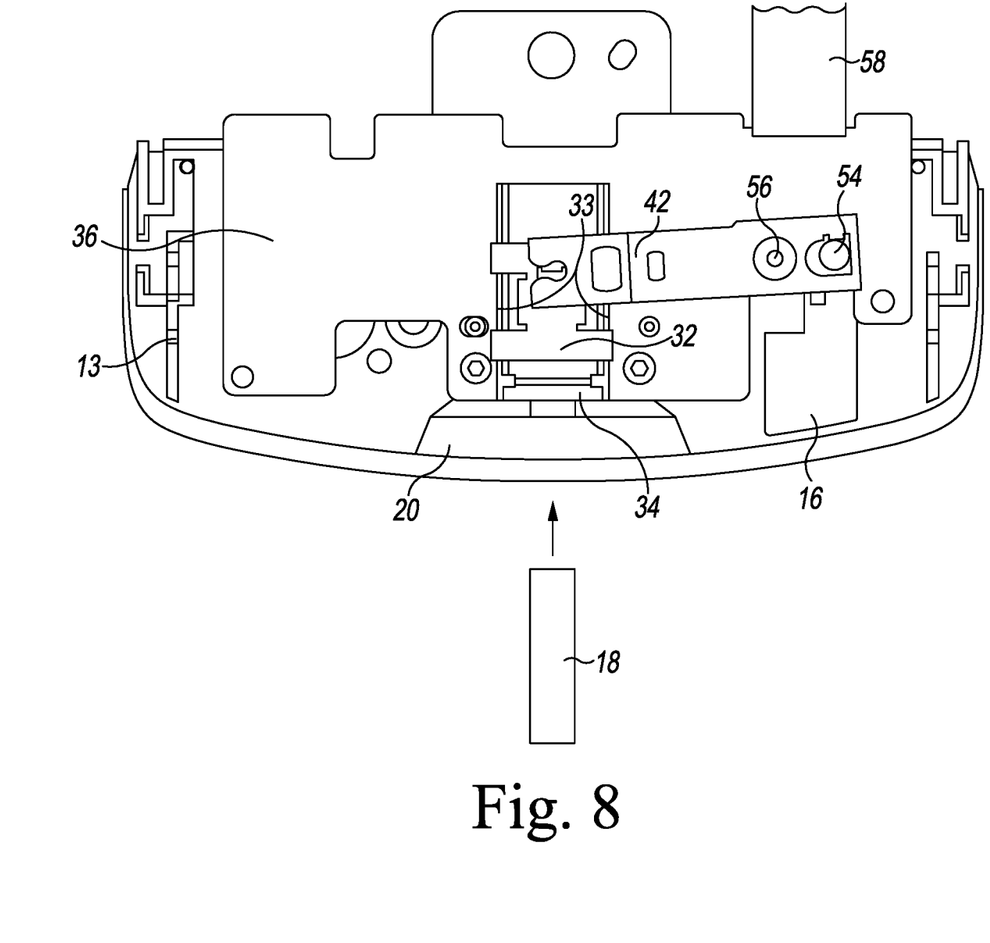
FIG. 8 is a view similar to the view of FIG. 2, but shows the test strip ejector button and ejector lever in the default/test or neutral position, and where a lever lock is not illustrated to provide better clarity of the ejector button and ejector lever.

FIG. 8 is a view similar to the view of FIG. 2, but shows the test strip ejector button and ejector lever in the default/test or neutral position, and where a lever lock is not shown.

Figure 9:
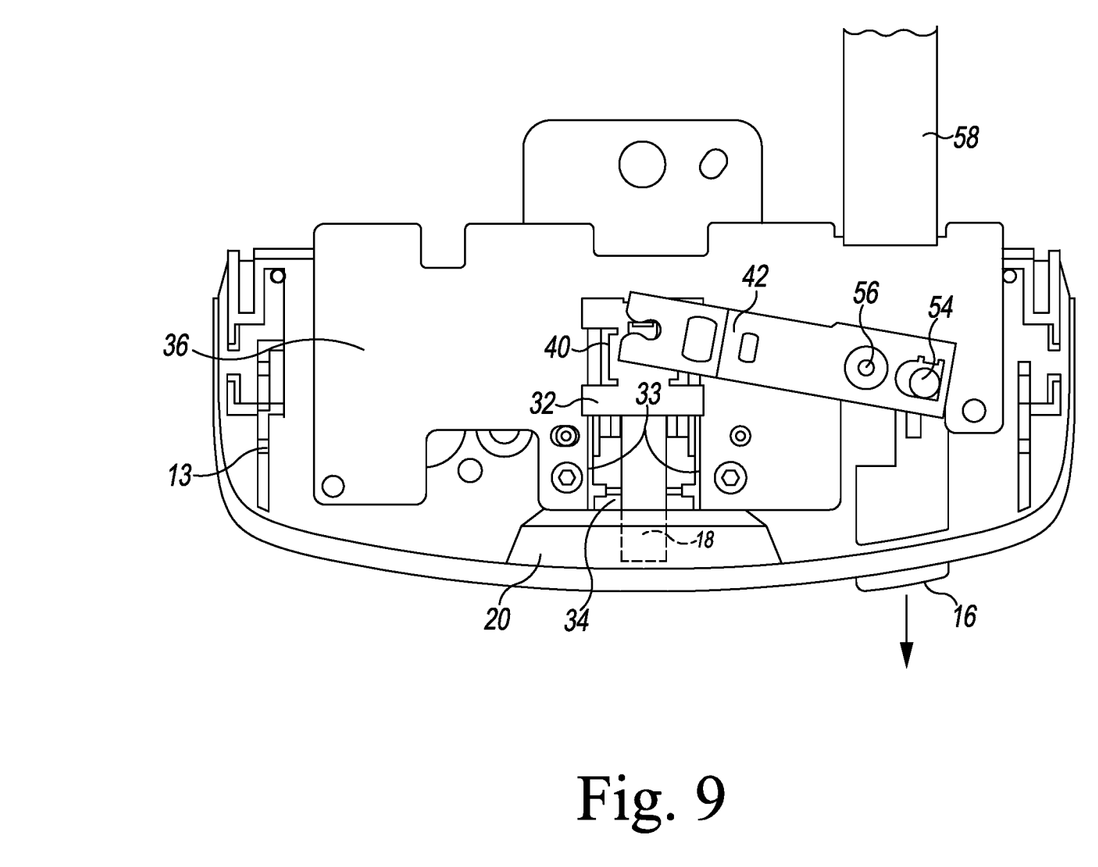
FIG. 9 is a view similar to the view of FIG. 8, but shows the device having a test strip inserted therein and showing the test strip ejector button and ejector lever displaced to the ejection ("ready to eject") position.

FIG. 9 is a view similar to the view of FIG. 8, but shows the device having a test strip inserted therein and showing the test strip ejector button and ejector lever displaced to the ejection position.

Figure 10:
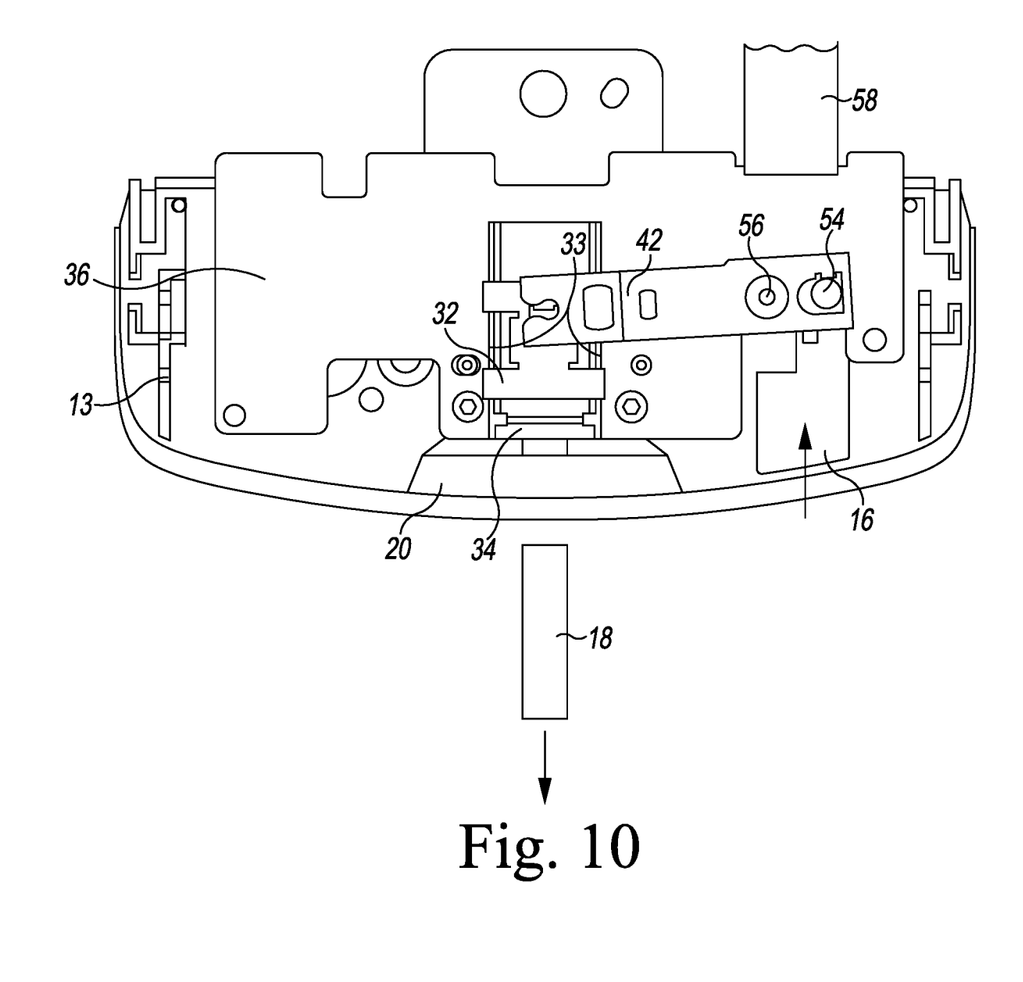
FIG. 10 is a view similar to the view of FIGS. 8 and 9, but shows the device after a test strip has been ejected therefrom and showing the test strip ejector button and ejector lever in the default/test or neutral position.

FIG. 10 is a view similar to the view of FIGS. 8 and 9, but shows the device after a test strip has been ejected therefrom and showing the test strip ejector button and ejector lever in the default/test or neutral position.

As shown in FIGS. 8-10, the ejector button mechanism including the ejector button 16 and the ejector lever 42 has two main positions. When the eject button 16 is fully depressed, then the sled 32 is moved outward as much as the mechanism allows. In this position, the test strip is disengaged from the electrical connectors of the device (i.e., is not in electrical contact with the electrical contacts), and the strip can fall out of the device if the device is oriented such that the strip port is pointing downward.

When the eject button is fully depressed as shown in FIG. 8 and the user inserts a test strip, the strip pushes the sled 32 inwardly via the two tabs of the sled. The sled then pushes the eject lever 42 through its third tab. The eject lever 42 rotates on its fulcrum and pushes the eject button outwardly by pushing on the eject button pin as described earlier to the position shown in FIG. 9.

As depicted in FIGS. 2 and 9, when the eject button protrudes outwardly from the device as shown, then the eject sled 32 has moved inward as much as the mechanism allows. In this position, the strip 32 can be fully inserted in the device, and the strip can be fully connected to the meter (typically electrically connected) in this embodiment. In other envisaged embodiments, other analyte measuring devices based on optical detection principles or other detection means not needing to make an electrical connection with a test strip could be utilized, and thus the test strip could simply be located within a designated test position or test region.

When a strip has already been inserted, and the eject button is pushed inwardly by a user, the pin in slot connection described above transfers the movement and force of the button to the eject lever 42. The eject lever 42 then rotates on its fulcrum and pushes the sled 32 outwardly and thus pushes the test strip 18 outwardly via the tabs of the sled as described earlier and as can be seen in FIG. 10.

Devices disclosed herein are configured to allow a test strip to be released or ejected from the device by pressing on a button, for improved hygiene, instead of a user having to manually pull the end of a test strip containing a biological sample. Also disclosed herein in some embodiments are devices which enable the eject button and sled to be quiet such as when a user is handling, shaking or carrying the device. This is accomplished by using the lever lock 50 to apply enough force to reduce the rattling noise of parts which would otherwise be freely moving parts (i.e., the eject button 16, the sled 32, and the lever arm 42) and to keep these parts in the position last utilized by the user.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A fluid testing medical device comprising a test strip eject mechanism comprising a sled for receiving and transporting an analyte test strip, wherein the sled slides to transport the test strip into and out of contact with a connector of the medical device, the strip eject mechanism comprising an actuation button and a lever having a distal end movably engaged with the button, the lever configured to rotate about a fulcrum, wherein the lever further comprises a proximal end movably engaged with the sled, the device configured such that a user's insertion of a test strip onto the sled and in an insertion direction into the device causes the sled to contact the lever arm and the lever arm to contact and move the actuation button in an outward direction of the medical device and into a position where the actuation button can be actuated by the user.

2. The device of claim 1 wherein the sled is configured to move in a sled movement distance, the actuation button is configured to move in an actuation button distance, and the ratio of the sled movement distance to the actuation button distance is from 1 to 5.

3. The device of claim 2 wherein the ratio of the sled movement distance to the actuation button distance is from 3 to 5.

4. The device of claim 2 wherein the ratio of the sled movement distance to the actuation button distance is from 3.7 to 3.9.

5. The device of claim 1 further comprising a lever lock which presses against and is frictionally engaged with the lever.

6. The device of claim 5 in which the lever lock is further configured to press against and be frictionally engaged with the sled.

7. The device of claim 5 in which the lever lock is further configured to press against and be frictionally engaged with the actuation button.

8. The device of claim 6 in which the lever lock is further configured to press against and be frictionally engaged with actuation button.

9. The device of claim 7 wherein the lever lock includes a tab that contacts the actuation button.

10. The device of claim 8 wherein the lever lock includes a tab that contacts the actuation button.

11. A fluid testing medical device comprising a test strip eject mechanism comprising a sled for receiving and transporting an analyte test strip, wherein the sled slides to transport the test strip into and out of contact with a connector of the medical device, the strip eject mechanism comprising an actuation button and a lever having a distal end movably engaged with the button, the lever configured to rotate about a fulcrum, wherein the lever further comprises a proximal end movably engaged with the sled, the device configured such that a user's actuation of the actuation button causes the actuation button to move the lever such that the lever rotates on its fulcrum and moves the sled in an outward direction to eject the test strip from the device, further comprising a lever lock which presses against and is frictionally engaged with the lever.

12. The device of claim 11 wherein the sled is configured to move in a sled movement distance, the actuation button is configured to move in an actuation button distance, and the ratio of the sled movement distance to the actuation button distance is from 1 to 5.

13. The device of claim 12 wherein the ratio of the sled movement distance to the actuation button distance is from 3 to 5.

14. The device of claim 12 wherein the ratio of the sled movement distance to the actuation button distance is from 3.7 to 3.9.

15. The device of claim 11 in which the lever lock is further configured to press against and be frictionally engaged with the sled.

16. The device of claim 11 in which the lever lock is further configured to press against and be frictionally engaged with the actuation button.

17. The device of claim 15 in which the lever lock is further configured to press against and be frictionally engaged with actuation button.

18. The device of claim 16 wherein the lever lock includes a tab that contacts the actuation button.

19. The device of claim 17 wherein the lever lock includes a tab that contacts the actuation button.

20. A method of using a fluid testing medical device comprising a test strip eject mechanism comprising a sled for receiving and transporting an analyte test strip, wherein the sled is configured to slide to transport the test strip into and out of contact with a connector of the medical device, comprising:
    configuring the strip eject mechanism to comprise an actuation button and a lever having a distal end movably engaged with the button, the lever configured to rotate about a fulcrum, wherein the lever further comprises a proximal end movably engaged with the sled; and
    inserting a test strip onto the sled and in an insertion direction into the device to thereby cause the sled to contact the lever arm and the lever arm to contact and move the actuation button in an outward direction of the medical device and into a position where the actuation button can be actuated by the user at a later time.

21. The method of claim 20 wherein the strip eject mechanism further comprises a lever lock which presses against and is frictionally engaged with the lever.

22. The method of claim 21 in which the lever lock is further configured to press against and be frictionally engaged with the sled.

23. The method of claim 21 in which the lever lock is further configured to press against and be frictionally engaged with the actuation button.

24. The method of claim 22 in which the lever lock is further configured to press against and be frictionally engaged with actuation button.

25. The method of claim 23 wherein the lever lock includes a tab that contacts the actuation button.

26. The method of claim 24 wherein the lever lock includes a tab that contacts the actuation button.

\* \* \* \* \*